(12) United States Patent
Lubenow et al.

(10) Patent No.: US 7,787,960 B2
(45) Date of Patent: Aug. 31, 2010

(54) LEAD ANCHORING ASSEMBLY

(75) Inventors: Timothy R. Lubenow, Hinsdale, IL (US); Kenny Kinyen Chinn, Castaic, CA (US); Christopher Ewan Gillespie, Stevenson Ranch, CA (US); John M. Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 112 days.

(21) Appl. No.: 11/706,702

(22) Filed: Feb. 15, 2007

(65) Prior Publication Data

US 2008/0196939 A1 Aug. 21, 2008

(51) Int. Cl.
*A61N 1/00* (2006.01)
(52) U.S. Cl. ..................................... 607/116
(58) Field of Classification Search .......... 607/116–117
See application file for complete search history.

(56) References Cited

U.S. PATENT DOCUMENTS

| | | |
|---|---|---|
| 3,176,690 A | 4/1965 | H'Doubler |
| 3,724,467 A | 4/1973 | Avery et al. |
| 3,821,957 A | 7/1974 | Riely et al. |
| 3,880,169 A | 4/1975 | Starr et al. |
| 4,219,027 A | 8/1980 | Lund et al. |
| 4,266,552 A | 5/1981 | Dutcher et al. |
| 4,276,882 A | 7/1981 | Dickhudt et al. |
| 4,287,891 A | 9/1981 | Peters |
| 4,516,584 A | 5/1985 | Garcia |
| 4,553,961 A | 11/1985 | Pohndorf et al. |
| 4,579,120 A | 4/1986 | MacGregor |
| 4,645,492 A | 2/1987 | Weeks |
| 4,672,979 A | 6/1987 | Pohndorf |
| 4,683,895 A | 8/1987 | Pohndorf |
| 5,059,746 A * | 10/1991 | Hayes et al. ................. 174/524 |
| 5,107,856 A | 4/1992 | Kristiansen et al. |
| 5,129,405 A | 7/1992 | Milijasevic et al. |
| 5,273,053 A | 12/1993 | Pohndorf |
| 5,476,493 A | 12/1995 | Muff |
| 5,484,445 A | 1/1996 | Knuth |
| 5,603,730 A | 2/1997 | Romkee |
| 5,628,780 A | 5/1997 | Helland et al. |
| 5,683,446 A | 11/1997 | Gates |
| 5,690,616 A * | 11/1997 | Mogg .......................... 604/174 |
| 5,746,722 A | 5/1998 | Pohndorf et al. |
| 5,843,146 A * | 12/1998 | Cross, Jr. ..................... 607/115 |
| 5,957,968 A | 9/1999 | Belden et al. |
| 6,002,969 A | 12/1999 | Machek et al. |
| 6,361,523 B1 * | 3/2002 | Bierman ...................... 604/174 |

(Continued)

FOREIGN PATENT DOCUMENTS

WO WO 01/68180 A1 9/2001

*Primary Examiner*—Scott M Getzow
*Assistant Examiner*—Amanda Patton
(74) *Attorney, Agent, or Firm*—Frommer Lawrence & Haug LLP; Bruce E. Black (57) ABSTRACT

An electrical lead anchoring assembly comprising a body comprising at least one recess and at least one channel there through for receiving at least one electrical lead, at least one arm pivotably coupled to the body and moveable between an open and a closed position wherein the arm is at least partially disposed within the recess such that the arm intrudes into the channel and frictionally abuts at least a portion of the length of electrical lead disposed in the channel to couple the lead to the body.

19 Claims, 8 Drawing Sheets

U.S. PATENT DOCUMENTS

| | | |
|---|---|---|
| 6,473,654 B1 * | 10/2002 | Chinn .................... 607/126 |
| 6,901,287 B2 * | 5/2005 | Davis et al. ................. 607/2 |
| 6,929,625 B2 | 8/2005 | Bierman |
| 6,972,003 B2 | 12/2005 | Bierman et al. |
| 7,499,755 B2 * | 3/2009 | Cross, Jr. ................ 607/117 |
| 2005/0182470 A1 * | 8/2005 | Cross ..................... 607/117 |
| 2005/0192594 A1 | 9/2005 | Skakoon et al. |
| 2006/0173520 A1 * | 8/2006 | Olson ..................... 607/115 |
| 2008/0097479 A1 * | 4/2008 | Boehlke et al. ............ 606/144 |
| 2008/0154326 A1 * | 6/2008 | Clyne ...................... 607/36 |

* cited by examiner

LEAD ANCHORING ASSEMBLY

FIELD OF THE INVENTION

The present invention generally relates to implantable tubes or cables, such as lead cables, for use with a medical device, and more particularly relates to an anchor for securing the tube or cable to the surrounding tissue.

BACKGROUND OF THE INVENTION

A variety of devices exist which make use of cables or tubes for delivering electrical signals, fluids, etc. from a medical device to a region of the body, or simply for holding device(s) in place. For example, electrical lead cables, i.e., leads or lead extensions that detachably connect to an electrical device or to other lead cables may deliver electrical stimulation to a nerve, muscle, or other tissue. For instance, numerous medical devices, such as neural stimulation devices, cardioverters, cardiac pacemakers, and defibrillators, commonly establish a connection between an implanted lead or lead extension (both will be referred to herein as lead cables or simply leads) and an implanted electronic package. In a typical pacemaker, the proximal end of a lead may be removably connected to a lead extension, which in turn is removably connected to an implantable pulse generator. The distal end of the lead, containing one or more electrodes, is typically inserted in or on the heart.

The most effective position of the electrodes or other devices at and/or along the distal end of the lead is commonly determined during surgery. Once the lead is implanted in this preferred position, it generally must be secured to surrounding tissue to prevent it from becoming dislodged. Accordingly, a lead anchor (also often referred to as a suture sleeve) that surrounds or is a part of a lead cable may be provided.

Various techniques and mechanisms have been proposed for securing implanted or partially implanted leads in a patient. In the early 1970's, "butterfly" type anchoring sleeves were provided with the lead, the anchoring sleeve being adapted to be sutured to a vein or underlying tissue. The anchoring sleeve was attached to the lead body during implantation, and protected the lead insulation from the stress of having a suture tied around it. When polyurethane leads were introduced in the late 1970's, the leads were frequently provided with a pre-fitted sleeve, typically formed of silicone rubber, to facilitate securing the lead with sutures. When installing the lead and sleeve, the physician would secure the lead by sliding the sleeve to a position near where the lead enters the vein, and suturing the sleeve to the vein or to underlying tissue.

Several examples of prior art suture sleeves are known in the prior art or are the subject of patent disclosures, including the following: U.S. Pat. No. 4,276,882 to Dickhudt et al. entitled "Lead Anchoring Device"; U.S. Pat. No. 4,516,584 to Garcia entitled "Suture Collar"; U.S. Pat. No. 4,553,961 to Pohndorf et al. entitled "Suture Sleeve with Structure for Enhancing Pacing Lead Gripping"; U.S. Pat. No. 4,672,979 to Pohndorf entitled "Suture Sleeve Assembly"; U.S. Pat. No. 4,683,895 to Pohndorf entitled "Suture Sleeve Anchoring Device"; U.S. Pat. No. 5,107,856 to Kristiansen et al. entitled "Multiple Lead Suture Sleeve"; U.S. Pat. No. 5,129,405 to Milijasevic et al. entitled "Vein Suture Collar"; U.S. Pat. No. 5,273,053 to Pohndorf entitled "Suture Sleeve With Lead Locking Device"; U.S. Pat. No. 5,476,493 to Muff entitled "Implantable Lead Having Self-Locking Suture Sleeve"; U.S. Pat. No. 5,603,730 entitled "Suture Sleeve for Implantable Lead"; U.S. Pat. No. 5,628,780 to Helland et al. entitled "Protective, Visible Suture Sleeve for Anchoring Tran venous Lead Bodies"; U.S. Pat. No. 5,683,446 to Gates entitled "Medical Electrical Lead Having an Anchoring Sleeve Retaining Device"; U.S. Pat. No. 5,746,722 to Pohndorf et al. entitled "Suture Sleeve With Circumferential Lead Locking Device"; U.S. Pat. No. 5,843,146 to Cross, Jr. entitled "Adjustable Medical Lead Anchor"; U.S. Pat. No. 5,957,968 to Belden et al. entitled "Suture Sleeve With Lead Locking Device"; and U.S. Pat. No. 6,473,654 to Chinn entitled "Lead Anchor".

Other types of securing devices are disclosed, for example, in the following references: U.S. Pat. No. 3,176,690 to H'Doubler entitled "Catheter Having Integral, Polymeric Flanges"; U.S. Pat. No. 3,724,467 to Avery et al. entitled "Electrode Implant for the Neuro-Stimulation of the Spinal Cord"; U.S. Pat. No. 3,821,957 to Riley et al. entitled "Retention Slide for Catheters and Other Tubular Materials"; U.S. Pat. No. 3,880,169 to Starr et al. entitled "Controlled Entry Pacemaker Electrode for Myocardial Implantation"; U.S. Pat. No. 4,266,552 to Dutcher et al. entitled "Lead Anchoring Bobbin"; U.S. Pat. No. 4,276,882 to Dickhudt et al. entitled "Lead Anchoring Device"; U.S. Pat. No. 4,287,891 to Peters entitled "Securing Device"; U.S. Pat. No. 5,484,445 to Knuth entitled "Sacral Lead Anchoring System"; U.S. Pat. No. 5,690,616 to Mogg entitled "Catheter Clamp"; U.S. Pat. No. 6,361,523 to Bierman entitled "Anchoring System for a Medical Article"; U.S. Pat. No. 6,929,625 to Bierman entitled "Medical Line Anchoring System"; and U.S. Pat. No. 6,972,003 to Bierman et al. entitled "Medical Anchoring System".

Known anchoring sleeves have several disadvantages. Early anchoring sleeves displayed a high rate of migration. While anchoring sleeves have improved over time, firm plastic anchoring sleeves such as those including relatively firm components that rotate relative to one another along the axis of the lead often acted as a fulcrum and allowed some motion such that patients could feel the placed device. Additionally, such devices likewise migrated over time.

While softer or silicone rubber suture sleeves offered some advantages over prior art, known silicone rubber suture sleeves likewise have several disadvantages. Sleeves which must be placed on the lead during manufacture can only be removed by cutting them off, as with a scalpel, when physicians do not wish to use them. This is considered undesirable, since there is a risk that the insulation of the lead would be damaged while the sleeve was being cut off. Moreover, when a silicone rubber suture sleeve becomes wet or infiltrated by moisture, the friction between the lumen of the sleeve and the lead may be reduced so much that the lead is allowed to slide, and is no longer anchored in place.

The lead anchor may require the physician to use, for instance, suture material to secure the anchor to the lead cable. Generally, lead anchors are configured to allow a physician to wrap suture(s) around and/or through the lead anchor multiple times, while securing the sutures to the adjacent tissue.

While securing the lead anchor to the lead cable and while securing the anchor (and thus the lead) to the adjacent tissue, a common problem is under-tightening of the sutures, which may result in inadequately securing the lead. Anchors typically stipulate the use of three separate sutures in order to keep the anchor tight against the lead. Even with three sutures, anchors often do not sufficiently secure the lead. Conversely, over-tightening of the sutures may result in stresses that can damage the wires within the lead cable and/or break the insulation, which may ultimately cause the lead to fail. Thus, the compression force created by using sutures depends on technique, skill level and accessibility of the suture sleeve in the wound site. Preferably, a lead anchor should provide a consistent clamping force that is not dependent of suturing technique, skill level or position in the wound site, and would preferably reduce the opportunities for any lead damage.

Securing the lead in place should be simple, to reduce surgical time, and evident, to limit chances for error. The lead anchor is preferably slidable along the lead so it may be positioned appropriately for different implant locations and for a variety of patient body types. Multiple lead anchors per lead cable may be useful in some situations.

The lead anchor is preferably compact and light-weight, and constructed of biocompatible materials. Once properly secured, the connection between the anchor and lead cable should be strong enough to resist pulling and any other forces that could unintentionally disconnect the lead cable from the surrounding tissue.

There exists a need in the art for a compact, easy to operate, fast, and reliable way to secure a tube or cable, such as a lead cable, to surrounding tissue that limits the likelihood of damage to the tube or cable.

BRIEF SUMMARY OF THE INVENTION

The invention provides a lead anchor assembly for securing lead cables, i.e., leads or lead extensions, or other cables or tubular members within a body, as, for example, for anchoring an epidural electrode to subcutaneous tissue. The assembly includes a body having at least one recess in which at least one securing arm is pivotably disposed to move between an open position wherein the arm is disposed at least partially without the recess, and a closed position wherein the arm is disposed at least partially within the recess. The body includes an outer face, and at least one channel extending between an inlet and an outlet to the outer face, a lead being inserted through the channel during placement in a patient. The at least one recess in which the arm is disposed opens at least partially into the channel, such that the arm intrudes into the channel to frictionally abut at least a portion of a length of lead disposed in the channel when the arm is disposed in the closed position to couple the lead to the body. Preferably, the arm is disposed in a plane that is parallel to the channel when the arm is disposed in the closed position in order to provide optimum force displacement and frictional engagement. The arm may include one or more protrusions which form the frictional face for abutting the lead when the arm is disposed in the closed position.

The arm is pivotably secured to the body by coupling structure. While the coupling structure may be of any appropriate design, the coupling structure typically comprises at least one protrusion extending from at least one of the arm or the body, and at least one corresponding recess in the other of the arm or the body, the second recess receiving the protrusion to pivotably couple the arm to the body. In an embodiment, the protrusion is in the form of a pin that extends into recesses or bores in both of the arm and the body. To facilitate x-ray or other similar confirmation of proper placement in the body, the pin may be formed of or coated with a radiopaque material. Alternately, another component of the assembly may be formed of or otherwise include a radiopaque material.

The assembly preferably includes a latch to retain the arm in a closed position after placement. The latch may be in the form of one or more protrusions or recesses or the like. The activation of the latch may provide audio or tactile confirmation of the proper closure of the assembly. In an embodiment of the invention, the arm is sufficiently flexible that it may be flexed to allow the arm to be moved from the closed to the open position to allow repositioning or the like of the assembly.

To facilitate securing the assembly to a patient, the anchoring assembly may include one or more bores or wells adapted to receive a suture. One or more sutures may be placed as desired by the surgeon. Placement options may include either or both through such bores or around the body of the assembly.

The inventive design may be constructed for utilization with more than one lead cable, if desired. A single arm may be provided for a plurality of cables, and/or a single arm may be provided for each cable.

In this way, the inventive lead anchor assembly offers a simple and secure method to lock onto and minimize any potential movement of a lead. Significantly, the lead anchor provides a consistent clamping force that is not dependent upon suturing technique, skill level or position in the wound site. The assembly is compact and easy to use. While the assembly may be easily secured to tissue using a single or multiple sutures, such sutures are not required in order to secure the assembly to a lead cable. Moreover, the assembly may be easily locked, unlocked and relocked in order to ensure accurate placement within a patient and to facilitate any revision surgery.

These and other objects and advantages of the invention will be apparent to those skilled in the art upon reading the following summary and detailed description and upon reference to the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
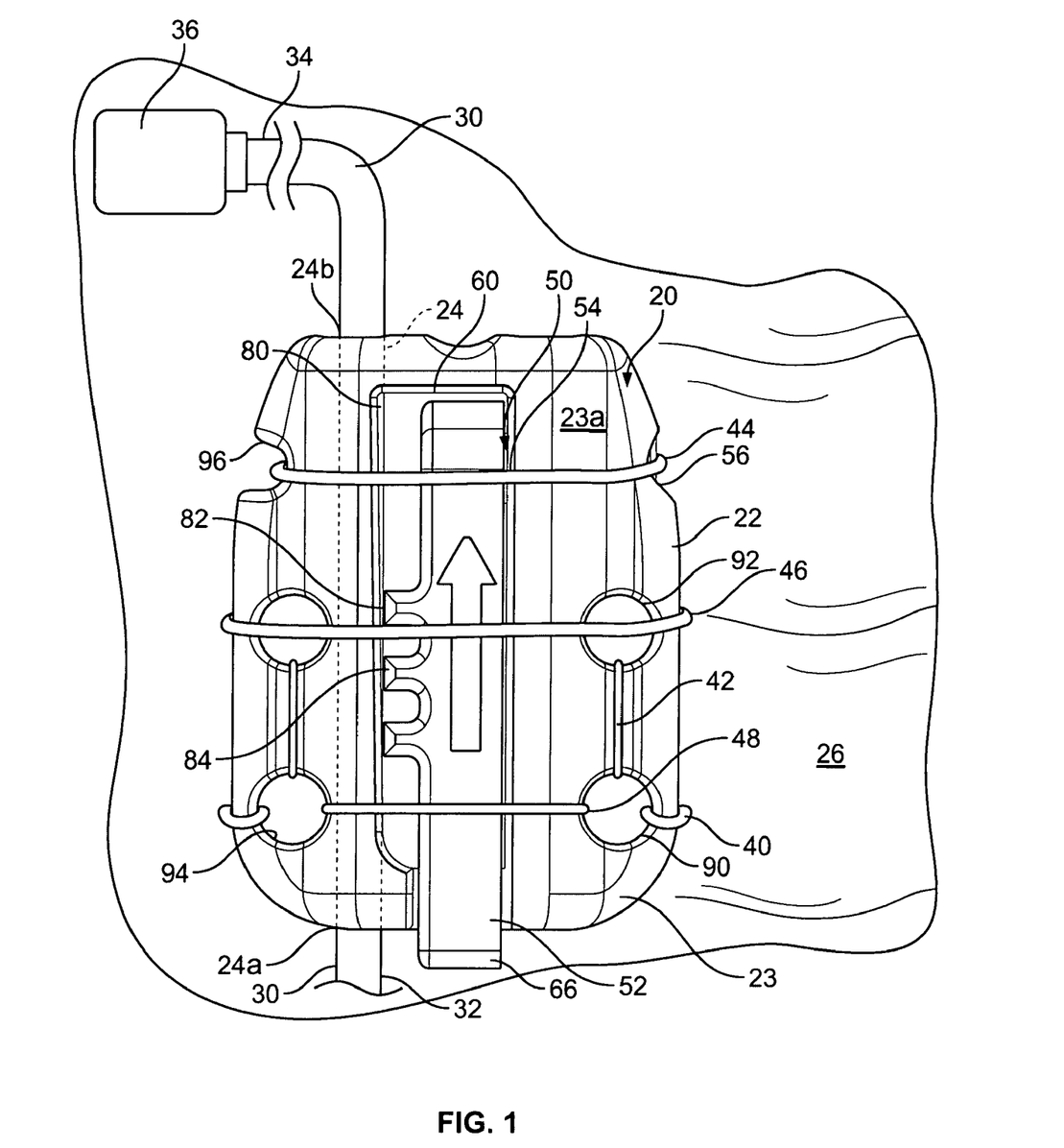
FIG. 1 is a schematic plan view of a lead anchor constructed according to teachings of the invention.

There is shown in FIG. 1, a schematic view of a lead anchor 20 comprising a body 22 having a longitudinally extending channel 24 through which an implantable lead cable 30 (i.e., lead, lead extension, or lead system) extends between an inlet 24a and an outlet 24b. It will be appreciated, however, that the lead anchor 20 could also be used to secure a drug-delivery tube, or other elongated cylindrical member, that has the same general form as the lead cable 30.

While the secured device 30 may have any appropriate structure, the illustrated lead cable 30 comprises a proximal end 32 and a distal end 34. In use, the distal end 34 is typically coupled to electrode or sensor array(s) (shown generally as reference numeral 36), while the proximal end 32 is typically coupled to a lead connector (not shown), which is typically connected to a lead extension or medical device (not shown in the drawings). Thus, the lead cable(s) 26 connect the distal electrodes/sensor(s) 36 to the medical device, thereby allowing the device to perform its intended function (e.g., neurostimulation, sensing, monitoring, or the like).

It will be appreciated by those of skill in the art that the lead cable 30 itself typically comprises a plurality of conductor wires enclosed or separated by one or more insulative sleeves, although alternate cable designs may be utilized. A typical lead cable 30 preferably has a circular outer diameter OD of about 1.35 mm (0.053 inch); although, it will be appreciated that the lead anchor 20 of the present invention may be sized to accommodate lead cables or tubes having diameters that are either smaller or larger than this.

Returning to FIG. 1, the lead anchor 20 is preferably disposed near the distal end 34 of the lead cable 30 to secure the lead cable 30 to adjacent body tissue (shown generally as reference numeral 26). The lead anchor 20 may be secured to the tissue by any appropriate means. In the illustrated embodiment, the lead anchor 20 can be secured by one or more of the sutures 40, 42, 44, 46, 48.

Figure 2:
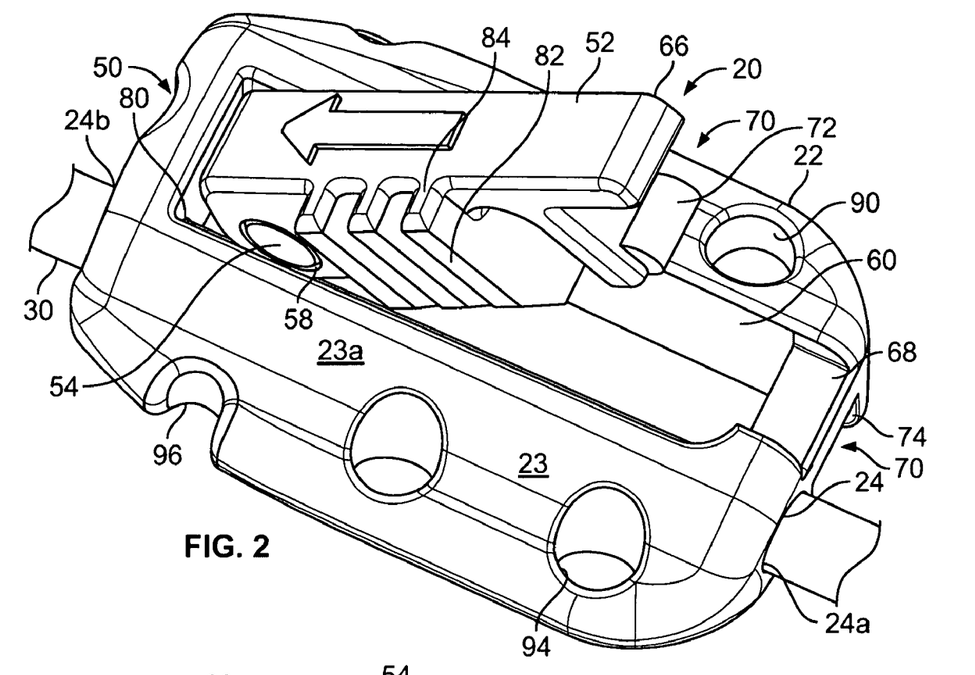
FIG. 2 is a perspective view of the lead anchor of FIG. 1 in an open position.
Figure 3:
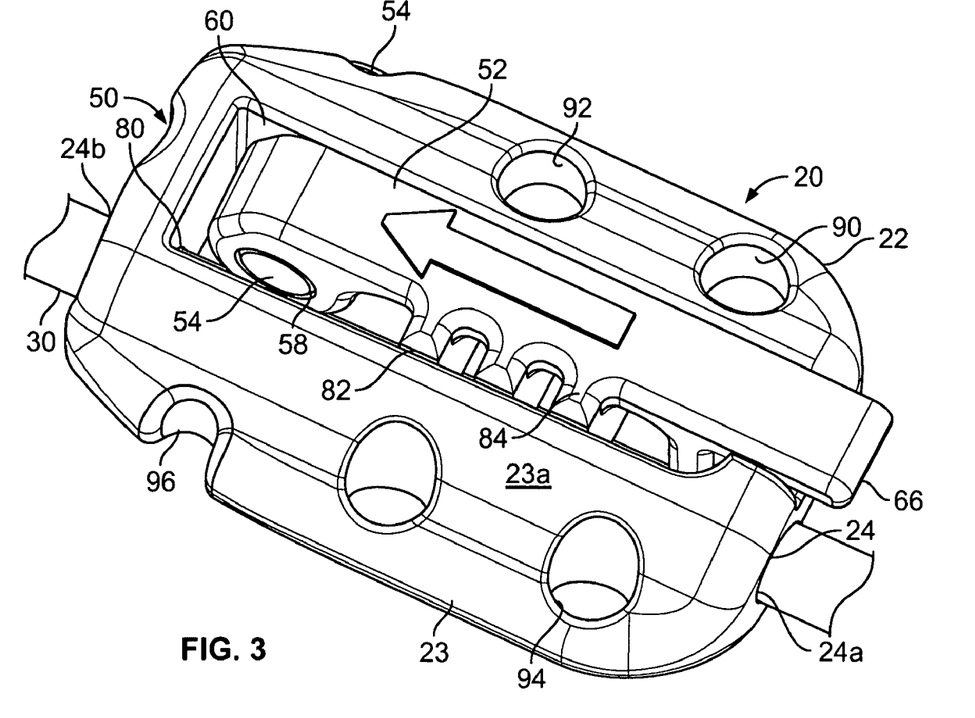
FIG. 3 is a perspective view of the lead anchor of FIGS. 1 and 2 in a closed position.
Figure 10:
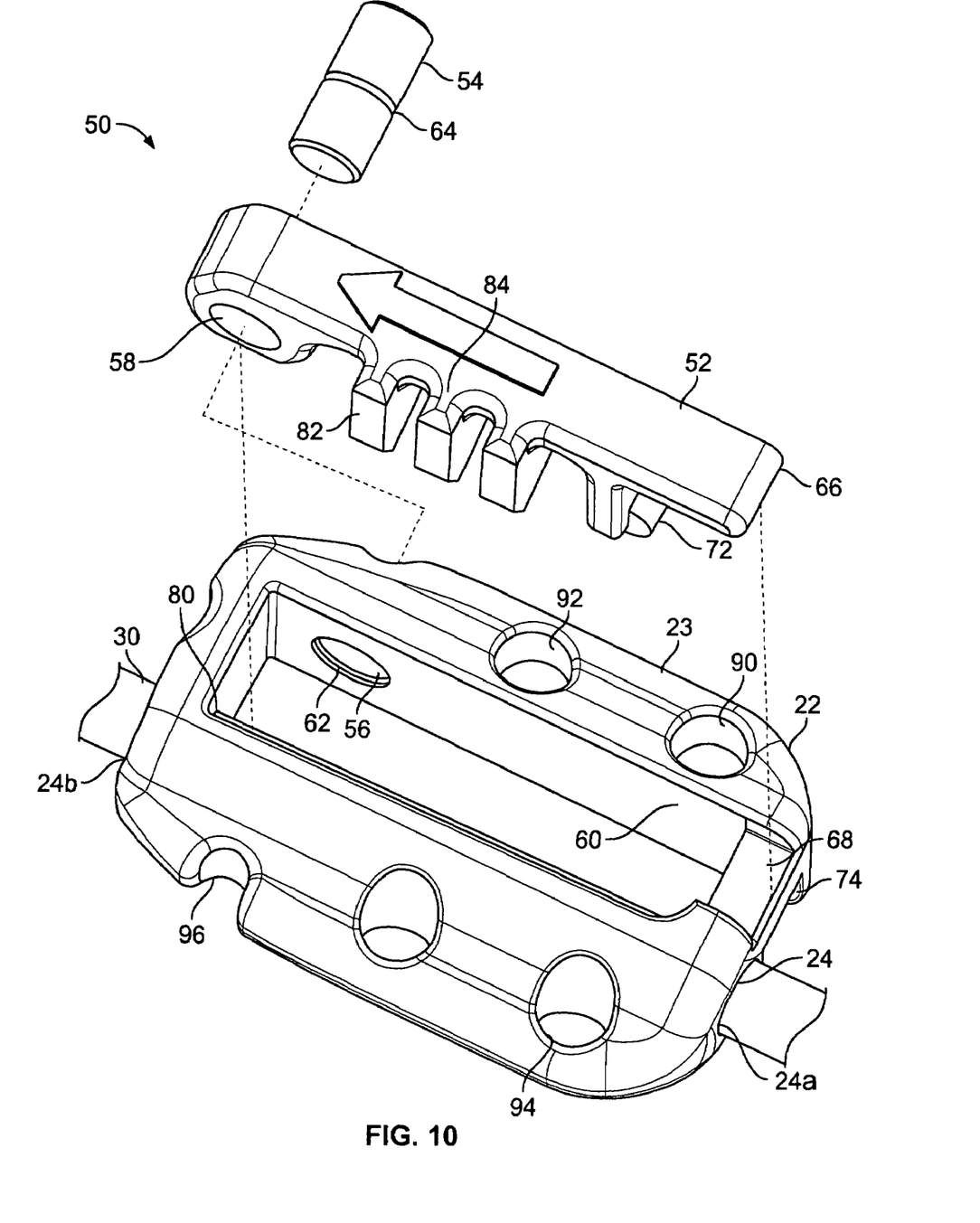
FIG. 10 is an exploded perspective view of the lead anchor of FIG. 1.

In accordance with an important aspect of the invention, the lead anchor 20 is provided with a coupling arrangement 50 for securing the lead anchor 20 to the lead cable 30. The coupling arrangement 50 comprises an arm 52 which is movable relative to the body 22 between a position wherein the arm 52 is disengaged from the lead cable 30 (as shown, for example, in FIG. 2) and a position wherein the arm 52 engages the lead cable 30 (as shown, for example, in FIGS. 1 and 3). In order to maintain the relationship of the arm 52 to the body 22, the coupling arrangement 50 comprises a coupling structure that pivotably couples the arm 52 to the body 22. While the coupling structure may comprise any appropriate mechanism, in the illustrated embodiment, the arm 52 is coupled to the body 22 by means of a pin 54, which extends through a recess, here in the form of a bore 56, in the body 22 and into a recess 58 in the arm 52. The relationship between the pin 54, the arm 52, and the body 22 is best shown in the exploded view of FIG. 10. As shown in dotted lines, the arm 52 is at least partially received within a recess 60 in the body 22 of the lead anchor 20. Although in the illustrated embodiment, when the arm 52 is disposed in a closed position, as shown in FIG. 3, the arm 52 is disposed substantially parallel to the channel 24, the arm 52 may be alternately disposed. In assembly, the bore 56 within the body 22 is aligned with the recess 58 extending at least partially into arm 52. The pin 54 is then press fit into the aligned bore 56 and recess 58 to pivotably retain the arm 52 to the body 22.

In the illustrated embodiment, the recess 58 in the arm 52 is in the form of a bore extending there through. Thus, while the recess 58 need only extend partially into the arm 52, it may extend entirely through the arm 52. Similarly, while the bore 56 is illustrated as extending entirely through a portion of the body 22, the bore 56 may likewise be in the form of a recess or depression, as permitted by the design of the coupling structure.

Likewise, the coupling structure may be of any appropriate design. By way of example only, the arm 52 or body 22 may include a protrusion that extends into a corresponding recess in the other of the arm or body, a spring loaded coupler may be compressed and placed in recesses in each of the arm 52 and body 22, or the arm 52 may be coupled to the body 22 by way of a living hinge. Those of skill in the art will appreciate that alternate arrangements thus fall within the purview of the invention.

Returning to the drawings, in order to maintain the pin 54 within position within the aligned bore 56 and recess 58, a protrusion 62 is provided within one of the bore 56 of the body 22 or the about the pin 54, while the other of the bore 56 and the pin 54 includes a corresponding recess 64. In the illustrated embodiment, an annular protrusion 62 extends into the bore 56 in the body 22, and the pin 54 includes an annular recess 64. During assembly, the annular protrusion 62 elastically deforms as the pin 54 slides through the bore 56 and into the recess 58 of the arm 52, the protrusion 62 essentially returning to its original position once disposed within the recess 64. In this way, the arm 52 is free to pivot relative to the body 22 as the pin 54 is retained within the bores 56 and recess 58 by disposition of the protrusion 62 within the recess 64. It will be appreciated by those of skill in the art that the annular snap-fit configuration of the protrusion 62 and the recess 64 minimizes residual stresses within the molded arm 52 and body 22 after assembly to prevent these parts from stress cracking over time. Once assembled, any residual loads/stresses between the press-fit pin 54 and a molded recess 58 in the arm 52 or a molded bore 56 in the body 22 are minimized or eliminated. As a result, the opportunity for stress cracks is minimized or eliminated following implantation in a patient.

It will further be appreciated by those of skill in the art that the protrusion 62 may be a singular annular protrusion, as illustrated, or it may alternately comprise any number of smaller individual protrusions that together provide a generally annular presentation. Alternately, the protrusion may be a single point protrusion that mates with a single recess to couple the pin, arm, and body.

In an embodiment of the invention, the pin 54 or an alternate component of the lead anchor assembly 20 is radiopaque such that the device may be identified on an x-ray or other monitoring arrangement. In this way, the use of such a monitoring arrangement may be particularly useful not only to ensure desired initial placement, but during revision surgery as well. For example, the pin 54 may be formed of a metal, such as titanium, for example. Alternately, the pin 54 or another of the components may be formed of a polyether ether ketone or the like, and may be made radiopaque through the use of barium sulfate or the like. The pin, arm, and body may likewise be made of any appropriate material, including polymeric materials, metallic material, such as titanium, or the like. Further, the components may be formed of one material and coated with a second, as, for example, when the body comprises a base formed of a first, relatively hard material, with an overcoat formed of a second, relatively soft material, such as urethane or silicone. In this way, the anchoring assembly 20 may allow for some degree of stress-form flexion to be absorbed, which may potentially produce less pain upon palpation or pressure.

Returning to the drawings, to facilitate manipulation of the arm 52 in placement by the surgeon, the arm 52 includes a flange 66 that extends from the distal end of the arm 52. In the embodiment illustrated in FIGS. 1-3, the arm 52 is substantially completely contained within the recess 54 within the body 22, but for a portion of the flange 66 that extends beyond the outer surface of the body 22. As best seen in FIGS. 1 and 3, a portion of the flange 66 is received in a depression 68 in the body 22. In this way, as a portion of the flange 66 extends beyond the outer surface 23of the body 22, the surgeon utilizes the flange 66 as a handle to pivot the arm 52 from the closed position of FIG. 3 to the open position of FIG. 2 if replacement or realignment is desired.

In order to ensure that the arm 52 is maintained in the closed position of FIG. 3 once proper placement has been made, the coupling arrangement may further comprise a latch 70. In the embodiment of FIGS. 1-3, the latch 70 includes a locking protrusion 72 that is received within a detent 74. In this embodiment, the locking protrusion 72 extends from the distal end of the arm 52, while the lower surface of the body includes the detent 74. In use, when the arm 52 is in the closed position, the locking protrusion 72 and the flange 66 are disposed on either side of and capture a portion of the body 22. In this way, the flange 66 limits the downward movement of the arm 52 through the recess 60 in the body 22, while the locking protrusion 72 limits the upward movement of the arm 52 from the recess 60 in the body 22.

Figure 13:
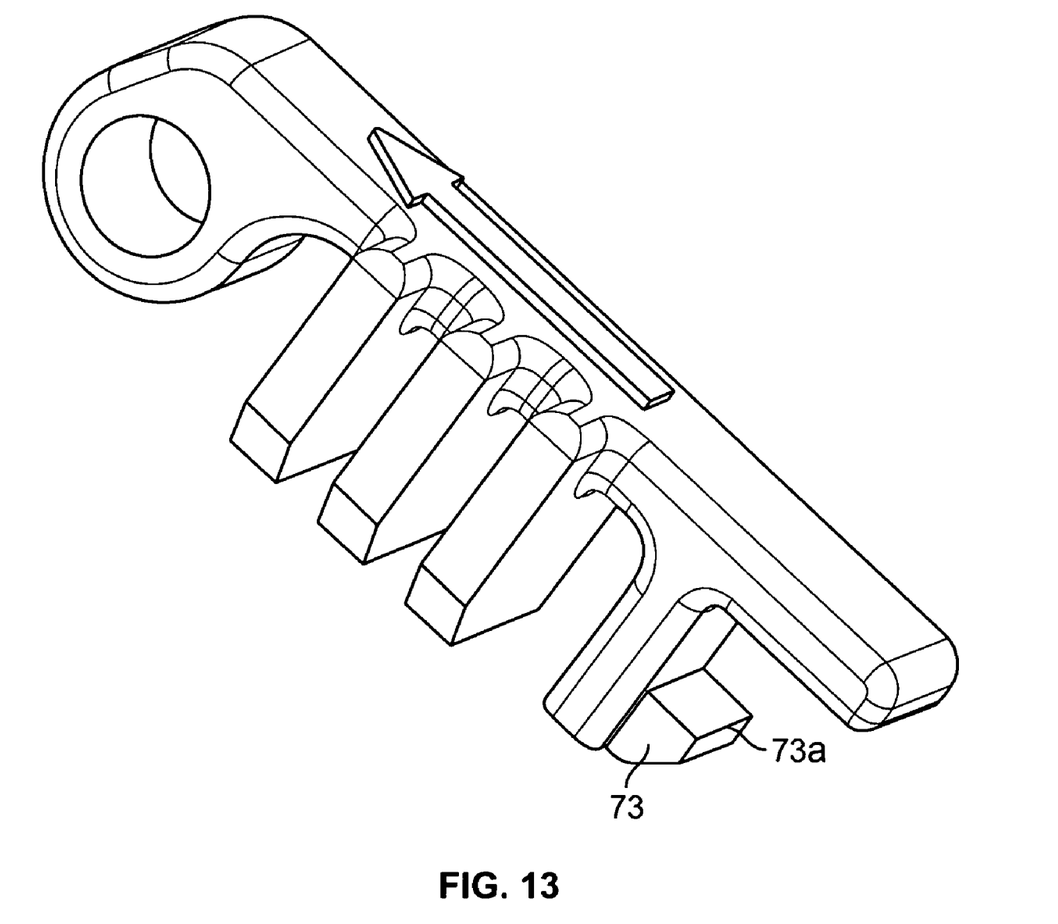
FIG. 13 is an enlarged perspective view of an alternate embodiment of a securing lever for a lead anchor constructed according to teachings of the invention.

The latch 70 itself may be of any appropriate design. For example, the locking protrusion 72 may be of an alternate design. It will be appreciated that the locking protrusion 72 includes radiuses along its upper and lower surfaces to facilitate advancing the locking protrusion 72 from the unlocked position to the locked position, and vice versa. The locking protrusion 73 could alternately have a sharp corner "hook" as shown, for example, in FIG. 13. It will be appreciated that the sharper corner 73a generally enhances retaining force in the locked position over the design shown in FIG. 11 if all other aspects of the design are essentially the same. By way of further example only, one or more protrusions from one of either the arm or the body may be disposed to abut a surface of or be received in a recess or detent in the other of the arm or body. More specifically, for example, protrusions (specific embodiment not illustrated) may be provided from the body 22 into the recess 60 along either side of the top surface of the arm 52 when the arm 52 is disposed in the closed position such that the protrusions capture the arm 52 in the closed position. By way of further example, a movable latch may be provided that holds the arm in the closed position. A specific example of such an arrangement may include a latch pivotably connected to the arm or the body, wherein the latch may be pivoted over the other of the arm or the body when the arm is disposed in the closed position. Other arrangements for locking the arm in a closed position likewise fall within the purview of the invention.

It will be appreciated that the latch 70 may likewise provide the surgeon with a tactile feedback and/or audible feedback to confirm proper closure of the lead anchor assembly 20. In the illustrated embodiment, as the arm 52 moves into the closed position and the locking protrusion 72 moves into the detent 74, there is a snapping as the arm 52 moves into the final closed position. In this way, in addition to the visual determination of proper placement and closure, the surgeon is provided with a tactile confirmation of proper closure. This tactile feedback may likewise be provided by alternate embodiments of the latch 70, such as those discussed above.

The surgeon may unlock the arm 52 from the body 22 by grasping the flange 66 either directly or using a tool or by "squeezing" the arm 52 and the body 22. By way of example only, the surgeon may utilize a tool such as a Kelly clamp, which is commonly available in surgical procedures. The surgeon can grasp the flange 66 and the distal end of the anchor body 22 with the tool and squeeze the arm 52, forcing the flange 66 toward the opposite, distal end of the anchor body 22, causing the arm 52 to arch upward, away from the body 22 to disengage the locking protrusion 72 from detent 74, thus allowing the arm 52 to pivot to the open position of FIG. 2.

To hold the lead cable 30 with the body 22, at least a portion 25 of the channel 24 extending through the body 22 opens into the recess 60 which receives the arm 52. In this way, the body 22 includes a recess opening 80 between the channel 24 and the recess 60. The arm 52 is disposed and sized such that a surface 82 of the arm 52 intrudes into the channel 24 when the arm 52 is disposed in the closed position of FIG. 3, and the arm 52 is at least partially disposed without the channel 24 when in the open position illustrated in FIG. 2. In this way, the lead cable 30 may be inserted into the inlet 24a, through the channel 24, and out of the outlet 24b when the arm 24 is disposed in the open position of FIG. 2. Conversely, when the arm 52 is disposed in the closed position of FIG. 3, at least the surface 82 of the arm 52 frictionally abuts at least a portion of the length of lead cable 30 disposed in the channel 24 to couple the lead cable 30 to the body 22.

Figure 11:
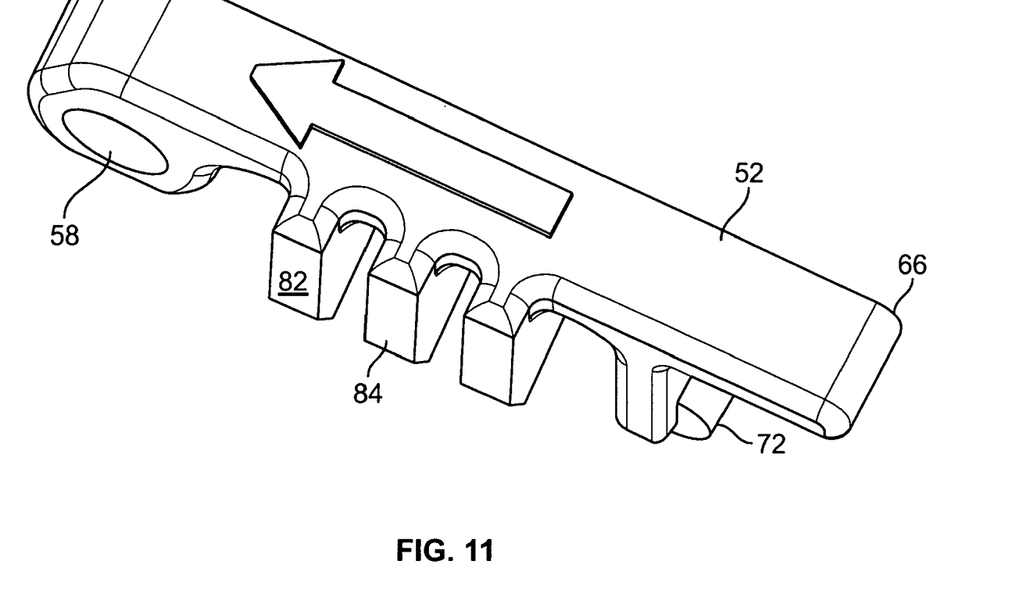
FIG. 11 is an enlarged perspective view of a securing lever of the lead anchor of FIGS. 1-3.
Figure 12:
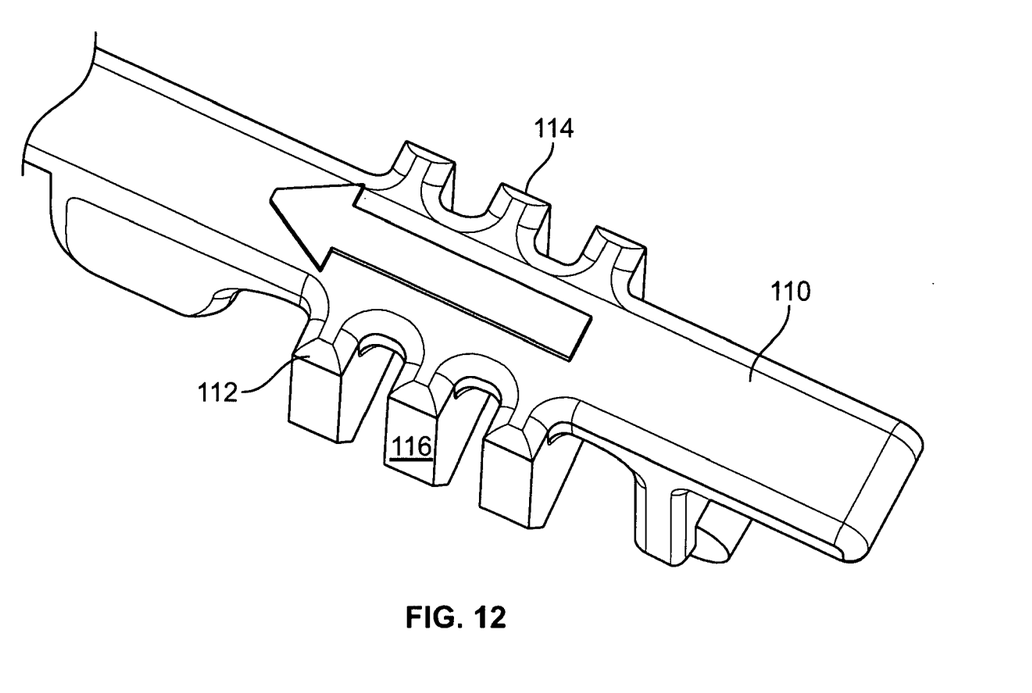
FIG. 12 is an enlarged perspective view of a securing lever of the lead anchor of FIGS. 4-9.

Referring to FIG. 11, the surface 82 of the arm 52 preferably is formed by the edges of one or more protrusions 84. These protrusions. 84 provide a series of frictional faces with the lead cable 30 extending through the channel 24, distributing the load applied to the lead cable 30 and providing a frictional engagement that minimizes or essentially prevents any movement between the lead cable 30 and the body 22. Significantly, the relative positions of channel 24 and the arm 52 in the closed position are determined such that the extent to which the surface 82 of the arm 52 applies a force to the lead cable 30 sufficient to retain the lead cable 30 in position, yet insufficient to damage the lead cable 30. Those of skill in the art will appreciate that the structure of the arm 52 may be other than that illustrated, so long as the arm 52 in a closed position causes a sufficient retaining force to be placed on the lead cable 30. Similarly, while the channel 80 is illustrated as a bore extending through the body 22, the channel 80 could alternately be or additionally include a recess also opening, for example, into a surface of the body 22, such as the top surface 23a shown in FIGS. 1-3.

To secure the lead cable 30 to the patient, the body 22 of the anchor assembly 20 is provided with one or more bores 90, 92, 94 or wells 96 that may be utilized to secure the anchor assembly 20 to tissue 26 by way of sutures 40, 42, 44, 46, 48. The positions of the bores and wells illustrated in the figures are provided by way of example only and may be alternately configure. Similarly, alternate numbers of bores or wells provided, only bores provided, or only wells provided, each of which may be alternately disposed.

As illustrated in FIG. 1, the sutures 40, 42, 44, 46, 48 may be disposed in any appropriate arrangement. Although a single suture, e.g., 40, may be sufficient to secure the anchor assembly 20 to the tissue 26, the surgeon may use any single suture type or combination of suture types if desired. For example, one or more sutures 40 may be disposed through a bore 90 and into tissue 26; one or more sutures 42 may be placed through a pair of bores 90, 92 and through the tissue 26; one or more sutures 44, 46 may be placed around the body 22, disposed either within or without the wells 96; one or more sutures 48 may be disposed through bores 90, 94 on opposite sides of the arm 52 such that the suture 48 extends across the arm 52. It will be appreciated by those of skill in the art that the disposition of sutures 44, 46, 48 across the upper surface of the arm 52 when disposed in a closed position provide the added benefit of further ensuring that the arm 52 remains in a closed position. Alternatively, when the sutures 44, 46, 48 are omitted, the arm 52 may then be pivoted to the open position of FIG. 2 to reposition the anchor assembly 20 along the lead cable 30, if so desired, as would be possible with the placement of sutures 40, 42 as illustrated. Inasmuch as a single suture is sufficient to secure the anchor assembly 20 to tissue, the currently preferred embodiment utilizes sutures of the type represented by sutures 40 and 42 in order to provide this added flexibility to the surgeon. Some surgeons may prefer to avoid wrapping the arm 52 to the anchor body 22 with surrounding sutures since they may desire the flexibility of repositioning the lead cable 30 relative to the anchor assembly 20 at a later time.

Figure 4:
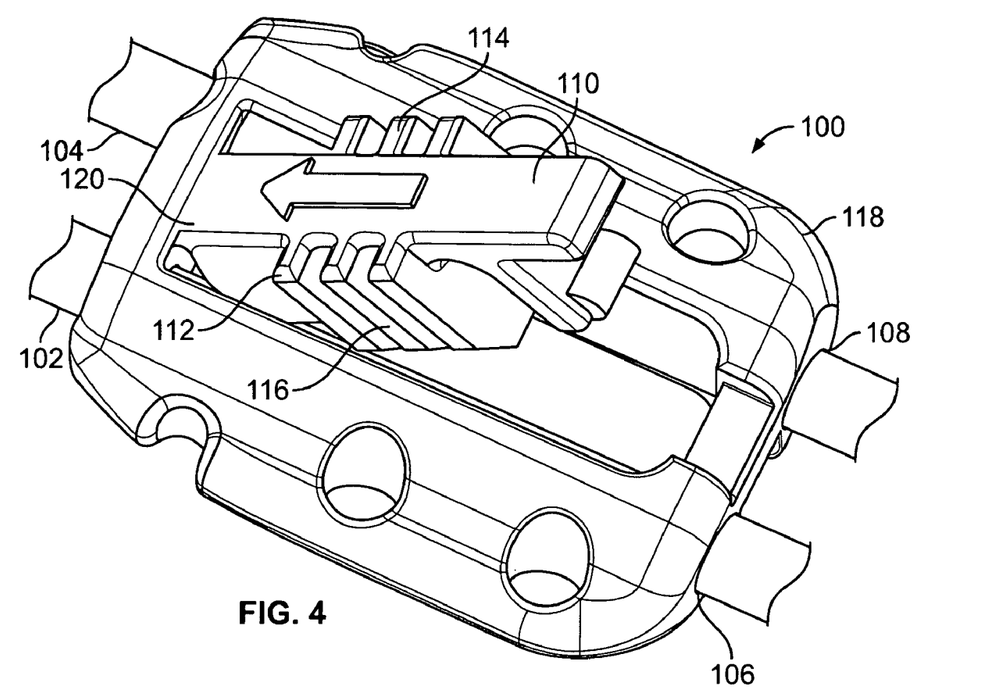
FIG. 4 is a perspective view of an alternate embodiment of a lead anchor constructed according to teachings of the invention, and in an open position.
Figure 5:
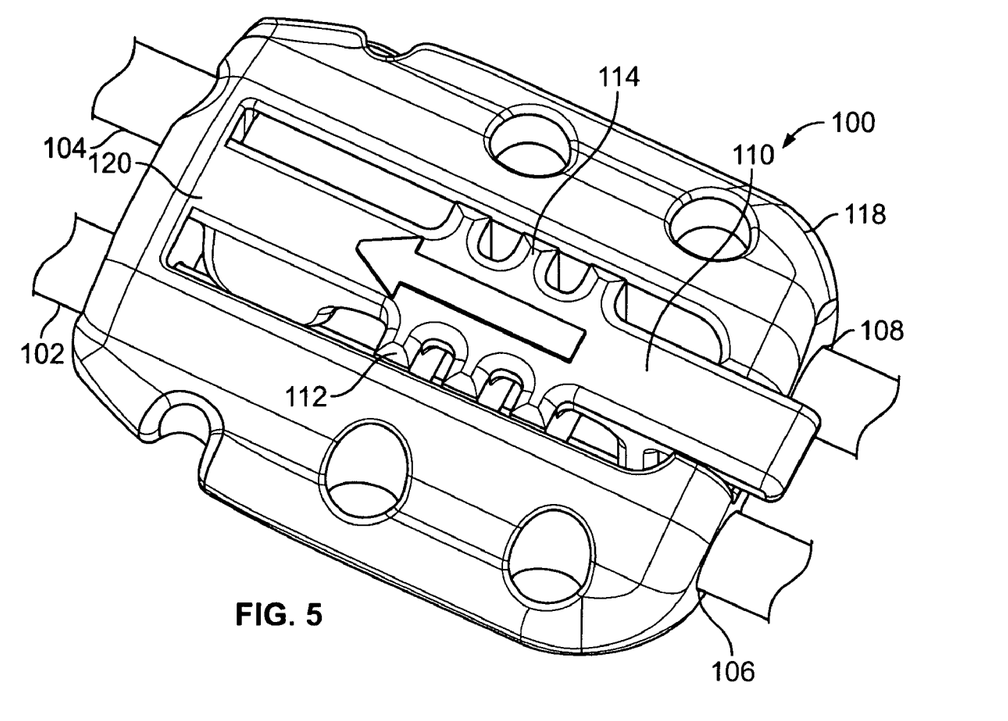
FIG. 5 is a perspective view of the lead anchor of FIG. 4 in a closed position.

According to another aspect of the invention, the coupling arrangement 50 may be utilized to retain more than one lead cable, if so desired. For example, referring to FIGS. 4 and 5, the lead anchor assembly 100 may couple two lead cables 102, 104 extending through a pair of channels 106, 108. While a separate arm may be provided for each lead cable 102, 104, in the illustrated embodiment, a single arm 110 is provided, the arm 110 preferably having one or more protrusions 112, 114 extending from either side to intrude into channels 106, 108. In this way, when the arm 110 is disposed in the closed position of FIG. 5, the protrusions present frictional faces 116 that abut the lead cables 102, 104 extending through the channels 106, 108 to retain the lead cables 102, 104 in the desired position relative to the body 118. In this embodiment, the arm 110 is pivotably coupled to the body 118 by way of a living hinge 120, although an alternate arrangement may be utilized. In other ways, the embodiment illustrated is essentially the same as that of FIGS. 1-3.

Figure 6:
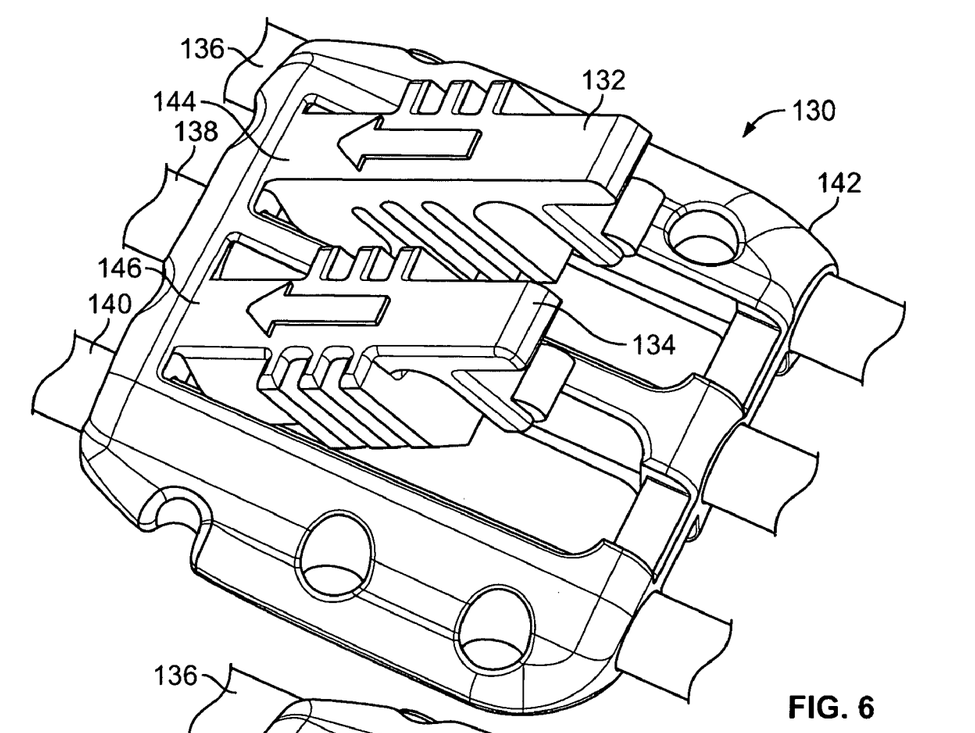
FIG. 6 is a perspective view of another alternate embodiment of a lead anchor constructed according to teachings of the invention, and in an open position.
Figure 7:
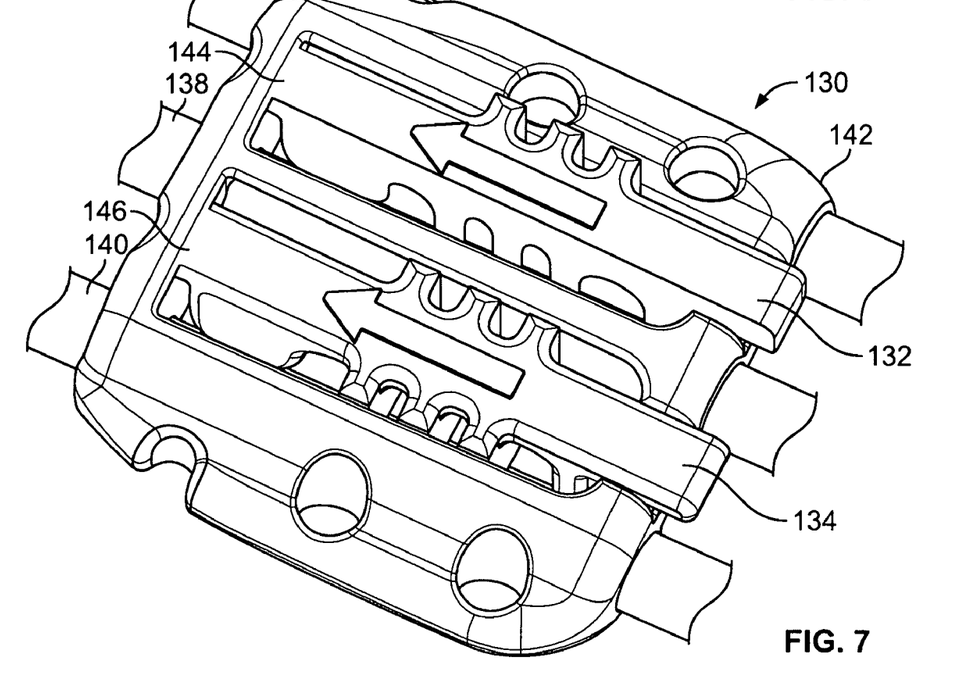
FIG. 7 is a perspective view of the lead anchor of FIG. 6 in a closed position.
Figure 8:
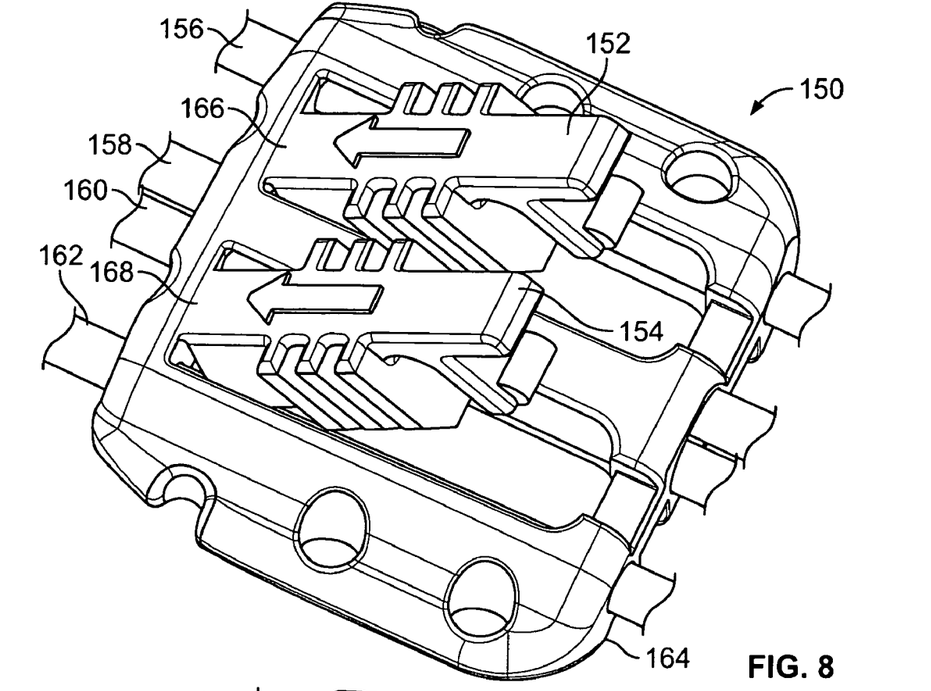
FIG. 8 is a perspective view of another alternate embodiment of a lead anchor constructed according to teachings of the invention, and in an open position.
Figure 9:
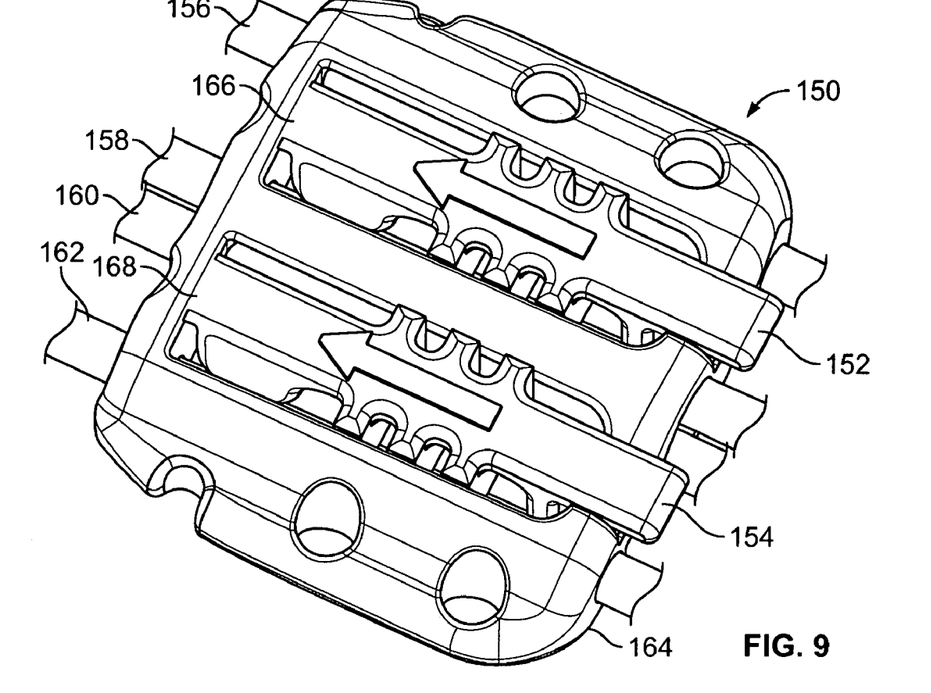
FIG. 9 is a perspective view of the lead anchor of FIG. 8 in a closed position.

Similarly, in the embodiment of FIGS. 6 and 7, the lead anchor assembly 130 includes a pair of arms 132, 134 and may be utilized to secure up to three lead cables 136, 138, 140. Although an alternate arrangement may be provided, in the illustrated embodiment, the first of the arms 132 has a structure similar to that illustrated in FIGS. 1-3 and engages a single lead cable 136, while the second arm 134 has a structure similar to that illustrate in FIGS. 4-5 and 11 and engages a pair of lead cables 138, 140. In the embodiment of FIGS. 8-9, the lead anchor assembly 150 similarly includes a pair of arms 152, 154, but may be utilized to secure up to four lead cables 156, 158, 160, 162, each arm 152, 154 being capable of securing a pair of the cables and having a structure similar to that illustrated in FIG. 11. As with the embodiment of FIGS. 4-5, the arms 142, 144, 152, 154 of the embodiments of FIGS. 6-9 are pivotably coupled to the bodies 132, 164 by way of living hinges 144, 146, 166, 168, although the arms may be alternately coupled if desired. Thus, it will be appreciated by those of skill in the art that a lead anchor assembly may be configured to retain either one or a multiple of cables, e.g., up to four or more, in accordance with teachings of the invention.

Lead anchors constructed according to teachings of the invention have numerous advantages over the prior art. Among other things, the lead anchor of the present invention has a relatively simple design and is easy to use. In use, the surgeon simply inserts the lead cable(s) through the channel(s) in the body of the anchor assembly. Once the lead cable(s) is positioned as desired, the surgeon moves the arm(s) to the closed position to secure the assembly to the lead cable(s). In moving the arm(s) to the closed position, the preferred locking of the arm to the body of the assembly provides the surgeon with a tactile confirmation that the arm(s) is securely closed. Moreover, the arm(s) and body may be manipulated with or without tools. Once positioned, the surgeon may secure the anchor assembly to tissue utilizing one or more sutures. If desired, one or more sutures may be placed around the entire assembly in order to further secure the arm(s) in the locked position. If, however, sutures are not placed about the periphery of the assembly while it is in the closed position, if the surgeon desires to move the lead cable(s) within the body, the arm(s) may be unlocked, the cable(s) moved as desired, and the arm(s) relocked. Alternately, the body of the anchor assembly may be sutured to tissue prior to initial locking of the arm(s) in a desired position. Accordingly, the present invention affords the surgeon enhanced control over prior devices. Thus, the lead anchor assembly provides a simple, yet reliable and easy-to-use approach for securing an implantable lead cable or similar structure, e.g. a tube, within a body. It provides a secure and evident connection to the lead cable without necessary use of a tool(s), thus reducing surgery time, risk of infection, and likelihood of error. With the anchor in place, the lead cable advantageously resists flexing and other forces, yet the anchor is compact and light-weight.

While the invention herein disclosed has been described by means of specific embodiments and applications thereof, numerous modifications and variations could be made thereto by those skilled in the art without departing from the scope of the invention set forth in the claims. By way of example only, other lead anchor shapes, sizes, and configurations will be apparent to those of skill in the art, such as an anchor lacking the advantages of suture holes. Additional alternatives will be apparent to those skilled in the art, from reading the specification and reviewing the drawings herein, without deviating from the spirit of the instant invention.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An anchoring assembly for anchoring an electrical lead having a length, the anchoring assembly comprising:
   (a) a body, said body comprising
      (i) an outer face,
      (ii) at least one inlet,
      (iii) at least one outlet,
      (iv) at least one channel, said channel extending between the inlet and the outlet for
   receipt of at least a portion of said length of lead, and
      (v) at least one recess bounded on at least four sides by a first pair of surfaces of the body, which oppose and face each other, and a second pair of surfaces of the body, which oppose and face each other and each connect the first pair of surfaces, said recess opening into said outer face and into said channel, and
   (b) at least one arm, said arm being pivotably coupled to said body and being moveable between an open and a closed position and bounded on at least four sides by the first pair of surfaces and the second pair of surfaces of the body, when in the closed position such that the arm intrudes into the channel, and said arm being at least partially disposed outside the recess while in the open position such that said length of lead may be inserted into the inlet, through the channel, and out of the outlet when the arm is disposed in the open position, the arm frictionally abutting at least a portion of the length of lead disposed in the channel when the arm is disposed in the closed position to secure the lead to the body,
   wherein the arm comprises a top surface that is perpendicular to a plane of rotation defined by movement of the arm from the open position to the closed position and that is on an exterior of the arm when the arm is in the closed position, a bottom surface opposite the top surface and at least one side connecting the top surface to the bottom surface, wherein at least a portion of the at least one side of the arm intrudes into the channel when the arm is in the closed position, and wherein at least the portion of the at least one side of the arm frictionally abuts at least the portion of the length of lead disposed in the channel when the arm is disposed in the closed position to secure the lead to the body.

2. The anchoring assembly of claim 1 wherein the arm is parallel to the channel when the arm is disposed in the closed position.

3. The anchoring assembly of claim 1 wherein the arm is disposed substantially within the recess when in the closed position such that it does not extend above the outer face.

4. The anchoring assembly of claim 1 wherein the arm further comprises at least one protrusion, said protrusion presenting a frictional face for abutting the lead when the arm is disposed in the closed position.

5. The anchoring assembly of claim 1 further comprising a coupling structure, said coupling structure being adapted and disposed to pivotably secure the arm to the body.

6. The anchoring assembly of claim 5 wherein the coupling structure comprises at least one protrusion extending from at least one of the arm or the body, and at least one corresponding, second recess in the other of said arm or said body, said second recess receiving said protrusion to pivotably couple the arm to the body.

7. The anchoring assembly of claim 1 further comprising at least one pin, said arm comprising at least one depression adapted to at least partially receive said pin to pivotably couple the arm to the body.

8. The anchoring assembly of claim 1 wherein the body comprises at least one of a bore or a well adapted to receive a suture.

9. The anchoring assembly of claim 1 further comprising a latch disposed to couple the arm to the body in the closed position.

10. The anchoring assembly of claim 9 further comprising means for providing at least one of an audible signal or tactile feedback of when the arm is moved to the closed position.

11. The anchoring assembly of claim 9 wherein the arm is sufficiently flexible such that the arm may be resiliently flexed to release said latch.

12. The anchoring assembly of claim 1 further comprising a plurality of arms, and wherein the body comprises a plurality of channels adapted to receive a plurality of leads.

13. The anchoring assembly of claim 1 wherein the body comprises a base formed of a first material and an over molding disposed over the base, the over molding comprising a second material that is softer relative to the first material of the base.

14. The anchoring assembly of claim 1, wherein the arm is substantially completely contained within the recess, and bounded on at least four sides by the body, when in the closed position.

15. The anchoring assembly of claim 1, wherein the arm comprises a handle region that extends beyond the recess and the body.

16. The anchoring assembly of claim 1, wherein a surface of at least one side of the arm frictionally abuts at least the portion of the length of lead, and wherein the surface of the at least one side of the arm is parallel to a plane of rotation defined by movement of the arm from the open position to the closed position.

17. The anchoring assembly of claim 1, further comprising a second channel extending between a second inlet and a second outlet in the body for receipt of at least a portion of a second lead, wherein a first side of the arm intrudes into the first channel and frictionally abuts at least a portion of the length of the first lead disposed in the first channel when the arm is disposed in the closed position, and wherein a second side of the arm intrudes into the second channel and frictionally abuts at least a portion of the length of the second lead disposed in the second channel when the arm is disposed in the closed position.

18. The anchoring assembly of claim 1, wherein the at least one recess is open to the exterior of the body on fifth and sixth sides that are perpendicular to a plane of rotation defined by movement of the arm from the open position to the closed position.

19. An anchoring assembly for anchoring an electrical lead having a length, the anchoring assembly comprising:
   (a) a body, said body comprising
      (i) an outer face,
      (ii) at least one inlet,
      (iii) at least one outlet, (iv) at least one channel, said channel extending between the inlet and the outlet for receipt of at least a portion of said length of lead, and
(v) at least one recess bounded on at least four sides by a first pair of surfaces of the body, which oppose and face each other, and a second pair of surfaces of the body, which oppose and face each other and each connect the first pair of surfaces, said recess opening into said outer face and into said channel, and
(b) at least one arm, said arm being pivotably coupled to said body and being moveable between an open and a closed position and bounded on at least four sides by the first pair of surfaces and the second pair of surfaces of the body, when in the closed position such that the arm intrudes into the channel, and said arm being at least partially disposed outside the recess while in the open position such that said length of lead may be inserted into the inlet, through the channel, and out of the outlet when the arm is disposed in the open position, the arm frictionally abutting at least a portion of the length of lead disposed in the channel when the arm is disposed in the closed position to secure the lead to the body,
wherein the arm comprises a top surface that is parallel to the outer face of the body and that is on an exterior of the arm when the arm is in the closed position, a bottom surface opposite the top surface and at least one side connecting the top surface to the bottom surface, wherein at least a portion of the at least one side of the arm intrudes into the channel when the arm is in the closed position, and wherein at least the portion of the at least one side of the arm frictionally abuts at least the portion of the length of lead disposed in the channel when the arm is disposed in the closed position to secure the lead to the body.

\* \* \* \* \*